United States Patent [19]

Hommeltoft et al.

[11] Patent Number: 5,672,741
[45] Date of Patent: Sep. 30, 1997

[54] PROCESS FOR THE HYDROLYSIS OF FLUORINATED SULPHONYL FLUORIDES

[75] Inventors: Sven Ivar Hommeltoft, Hillerød; Ole Ekelund, Lyngby, both of Denmark

[73] Assignee: Haldor Topsoe A/S, Denmark

[21] Appl. No.: 593,143

[22] Filed: Feb. 1, 1996

[30] Foreign Application Priority Data

Feb. 8, 1995 [DK] Denmark ................... 0145/95

[51] Int. Cl.$^6$ ................................. C07C 303/32
[52] U.S. Cl. ................................. 562/113
[58] Field of Search ................................. 562/113

[56] References Cited

U.S. PATENT DOCUMENTS

| | | |
|---|---|---|
| 1,189,562 | 7/1916 | Groehn et al. |
| 2,732,398 | 1/1956 | Brice et al. ........................ 260/503 |
| 2,877,267 | 3/1959 | Van Dyke Tiers et al. ........... 260/543 |
| 3,542,864 | 11/1970 | Koshar ................................ 260/543 |
| 3,919,295 | 11/1975 | Wechsberg et al. ................. 260/501 |

FOREIGN PATENT DOCUMENTS

| | | |
|---|---|---|
| 1573537 | 7/1969 | France . |
| 1668584 | 2/1968 | Germany . |
| 1912738 | 3/1969 | Germany . |
| 2725211 | 6/1977 | Germany . |
| 4208364 | 3/1992 | Germany . |
| 4218562 | 6/1992 | Germany . |
| 4226758 | 8/1992 | Germany . |

*Primary Examiner*—Joseph Conrad
*Attorney, Agent, or Firm*—Ostrolenk, Faber, Gerb & Soffen, LLP

[57] ABSTRACT

A process for base hydrolysis of a fluorinated sulphonyl fluoride by treatment of the fluoride with at least one mole equivalent of water in a basic solvent for a sufficient time to obtain a salt of a corresponding fluorinated sulphonic acid with the basic solvent and separating the obtained salt from the solution, wherein the basic solvent is selected from the group of tertiary amines.

5 Claims, No Drawings

PROCESS FOR THE HYDROLYSIS OF FLUORINATED SULPHONYL FLUORIDES

The present invention is in general directed to preparation of fluorinated sulphonyl acid compounds. In particular, the invention concerns certain improvements in the hydrolysis of fluorinated sulphonyl fluorides being an important step in the preparation of fluorinated sulphonic acids.

Fluorinated sulphonyl fluorides may be prepared in several ways, like electrochemical fluorination of corresponding alkane sulphonyl halides or cyclic sulphones in anhydrous HF (U.S. Pat. No. 2,732,398, DE Offenlegungsschrift No. 2,725,211, DE Offenlegungsschrift No. 1,912,738, DE Offenlegungsschrift No. 4,208,364, DE Offenlegungsschrift No. 4,218,562 and DE Offenlegungsschrift No. 4,226,758). Furthermore, it is known to obtain perfluorinated sulphonyl fluorides by addition of sulphuryl difluoride or sulphuryl chloride fluoride to the perfluoro-olefins (U.S. Pat. No. 1,189,562, U.S. Pat. No. 2,877,267, DE Auslegenschrift No. 1,668,584, FR Patent No. 1,573,537, U.S. Pat. No. 3,542,864).

Hydrolysis of sulphonyl fluorides is usually performed by contacting the fluorides with an aqueous alkaline solution, such as solutions of KOH, NaOH or $NH_4OH$. The product from the hydrolysis step is thereby an aqueous solution of salts, from which a salt of the fluoroalkane sulphonic acid can be recovered as a solid. The large excess of water used in the known processes may cause corrosion on process equipment. Additionally, the low solubility of fluorinated sulphonyl fluorides in aqueous solutions limits the hydrolysis rate resulting in a relatively slow conversion. The salt has afterwards to be dried before further processing. Solids handling involved thereby complicates the process.

It has now been found that the hydrolysis rate during hydrolysis of fluorinated sulphonyl fluorides may be increased and excess of water avoided, when carrying out the hydrolysis process in a solution with an amine solvent being inert with respect to amide formation under reaction conditions employed.

Pursuant to this finding, this invention provides a process for base hydrolysis of a fluorinated sulphonyl fluoride by treatment of the fluoride with at least one mole equivalent of water in a basic solvent for a sufficient time to obtain a salt of a corresponding fluorinated sulphonic acid with the basic solvent and separating the obtained salt from the solution, wherein the basic solvent is selected from the group of tertiary amines.

Because of the higher solubility of fluorinated alkyl sulphonyl fluorides in tertiary amine solvents, the hydrolysis reaction proceeds at a much higher rate than in aqueous solutions, even when water is present in the solution in only stoichiometric amounts.

As further an advantage of the invention, understoichometric water concentrations in the solution lead to substantially anhydrous hydrolysis products.

As mentioned above, suitable amines for use as solvent in the inventive hydrolysis process are the tertiary amines, which do not form amides with the hydrolysed fluoride acid compounds. Preferred are those tertiary amines, which form a low melting salt with the hydrolysis product. Presently, most preferred amines are $C_2$–$C_8$ trialkyl amines.

EXAMPLE 1

0.51 g (28.3 mmole) water was added within a period of 14 minutes to a homogeneous mixture of 8.18 g (32.5 mmole) perfluoropropane 1-sulphonyl fluoride ($CF_3CF_2CF_2SO_2F$) and 12 ml (133.2 mmole) trimethylamine. Instant precipitation of salt was observed upon addition of the first drop of water. After addition of water, excess of reagents was removed by passing a stream of nitrogen through the reaction mixture. 7.38 g of a white salt mixture of $CF_3CF_2CF_2SO_3HNMe_3$ and $H_nF_{n+1}HNMe_3$ and containing 0.6–1.1% water were recovered after removal of unreacted amine and sulphonyl fluoride.

EXAMPLE 2

To a homogeneous mixture of 16.95 g (67.2 mmole) perfluoropropane 1-sulphonyl fluoride ($CF_3CF_2CF_2SO_2F$) and 37.5 ml (270.5 mmole) triethylamine, 1.05 g (58.3 mmole) water was added within a period of 35 minutes. During addition, the temperature increased from 16° C. to 70° C. caused by heat of reaction. A liquid salt phase separated from the solution. After addition of water, excess of reagents was removed bypassing a stream of nitrogen through the reaction mixture. 24.18 g of brownish viscous liquid salt mixture of $CF_3CF_2CF_2SO_3HNEt_3$ and $F(HF_n)HNMe_3$, containing less than 0.01% water were recovered after removal of unreacted amine and sulphonyl fluoride.

EXAMPLE 3

To a homogeneous mixture of 8.19 g (32.5 mmole) perfluoropropane 1-sulphonyl fluoride ($CF_3CF_2CF_2SO_2F$) and 10.5 ml (129.8 mmole) pyridine, 0.52 g (28.9 mmole) water was added over a period of 11 minutes. The temperature increased from 19° C. to 37° C. by heat of reaction. 10.76 g of a yellow crystalline solid consisting of a mixture of $CF_3CF_2CF_2SO_3HNC_5H_5$ and $F(HF_n)HNC_5H_5$ with a water content of 0.1–0.5% were recovered after removal of unreacted amine and sulphonyl fluoride by distillation.

EXAMPLE 4

To a homogeneous mixture of 24.66 g (97.8 mmole) perfluoropropane 1-sulphonyl fluoride ($CF_3CF_2CF_2SO_2F$) and 18 ml (130 mmole) triethylamine a solution of 1.5 g (83.2) mmole) water in 18 ml triethylamine was added dropwise within a period of 36 minutes. The temperature increased initially from 27° C. to 41° C. due to the heat of reaction. Further temperature increase was prevented by cooling the reaction mixture in an ice bath. Additional 18 ml triethylamine were added and 41.4 g of a viscous liquid salt phase (mixture of $CF_3CF_2CF_2SO_3HNEtF$ and $FHNEt_3$, $\rho \approx 1,24$ g/ml) with a water content of less than 10 ppm were isolated.

EXAMPLE 5

To 18.4 g (61 mmole) perfluorobutane 1-sulphonyl fluoride ($CF_3CF_2CF_2CF_2SO_2F$) were added to a solution of 0.94 g water (52.2 mmole) in 34 ml triethylamine ($Et_3N$). By heat of reaction the temperature increased to 65° C., at which point the solution was cooled to below 60° C., while rest of the water/amine solution was added. 28.9 g of a salt mixture of $CF_3CF_2CF_2CF_2SO_3HNEt_3+FHNEt_3$ ($\rho \approx 1,21$ g/ml, water content less than 100 ppm) were isolated as a separate phase.

EXAMPLE 6

20.8 g (69 mmole) perfluorobutane 1-sulphonyl fluoride ($CF_3CF_2CF_2CF_2SO_2F$) were reacted with 1.1 ml (61 mmole) water in tributylamine ($Bu_3N$) solution (65 ml, 273 mmole) as described above, resulting in recovery of 43.7 g of a salt mixture of $CF_3CF_2CF_2CF_2SO_3HNBu_3+FHNBu_3$ as viscous liquid ($\rho \approx 1,19$ g/ml) with a water content of 100 ppm.

EXAMPLE 7

To a stirred solution of 24.2 g (48 mmoles) perfluorooctane 1-sulphonyl fluoride ($CF_3(CF_2)_7SO_2F$) in 46 ml (193 mmole) tributylamine, 0.76 g (42.2 mmole) water was added. After 10 minutes, the temperature had risen to 85° C. and the mixture was cooled in an ice bath. A salt mixture was separated in form of a dense ($\rho \approx 1.37$ g/ml) viscous liquid with a water content of 40 ppm. Yield: 35.4 g salt mixture ($CF_3(CF_2)_7SO_3HNBu_3$+$FHNBu_3$).

EXAMPLE 8

Hydrolysis of trifluoromethane sulphonyl fluoride ($CF_3SO_2F$) was carried out in a column with down flowing amine water mixture as follows: 130 ml (940 mmoles) triethylamine ($N(Et)_3$) and 1.71 ml (95 mmoles) water were added to a 250 ml three necked flask equipped with a 50 cm long column filled with 6 mm glass Raschig rings. The content of the flask was circulated from the flask to the top of the column with a peristaltic pump and allowed to flow down through the column and back into the flask. Thereby, the packing material in the column was wetted with the content of the flask throughout the experiment. The flask was connected to a freezing trap for collection of possible unreacted sulphonyl fluoride. 16.3 g (107 mmoles) gaseous trifluoromethane sulphonyl fluoride were led to the middle of the column during a period of 30 minutes. During addition, the temperature was 20°–32° C. When the addition was completed, the content of the flask was separated into two phases. A heavy phase containing 24 g of a salt mixture ($CF_3SO_3HNEt_3$+$FHNEt_3$) was isolated as a yellowish viscous liquid ($\rho \approx 1.15$ g/ml) with a water content of 90 ppm. A small portion (less than 0.5 g) of unconverted product was left in the freezing trap.

We claim:

1. A process for base hydrolysis of a fluorinated sulphonyl fluoride by treatment of the fluoride with at least one mole equivalent of water in a basic solvent for a sufficient time to obtain a salt of a corresponding fluorinated sulphonic acid with the basic solvent and separating the obtained salt from the solution, wherein the basic solvent is selected from the group of tertiary amines.

2. The process of claim 1, wherein the fluorinated sulphonyl fluoride comprises a fluorinated alkane sulphonyl fluoride.

3. The process of claim 1, wherein the fluorinated sulphonyl fluoride comprises a perfluorinated sulphonyl fluoride.

4. The process of claim 1, wherein the tertiary amines comprise $C_2$–$C_8$ trialkyl amines.

5. The process of claim 1, wherein the tertiary amines comprise pyridine.

* * * * *